US012690930B2

(12) United States Patent
Aouachria et al.

(10) Patent No.: US 12,690,930 B2
(45) Date of Patent: Jul. 28, 2026

(54) COLLABORATIVE MEDICAL ROBOT FOR SECURE INSTRUMENT GUIDANCE

(71) Applicant: Quantum Surgical, Montpellier (FR)

(72) Inventors: Mohammed Foued Aouachria, Montpellier (FR); Lucien Blondel, Montpellier (FR); Bertin Nahum, Castelnau-le-Lez (FR); Fernand Badano, Lyons (FR)

(73) Assignee: Quantum Surgical, Montpellier (FR)

( * ) Notice: Subject to any disclaimer, the term of this patent is extended or adjusted under 35 U.S.C. 154(b) by 290 days.

(21) Appl. No.: 18/551,001

(22) PCT Filed: Mar. 14, 2022

(86) PCT No.: PCT/FR2022/050456
§ 371 (c)(1),
(2) Date: Sep. 18, 2023

(87) PCT Pub. No.: WO2022/195210
PCT Pub. Date: Sep. 22, 2022

(65) Prior Publication Data
US 2024/0156553 A1      May 16, 2024

(30) Foreign Application Priority Data
Mar. 17, 2021    (FR) .................................. FR2102647

(51) Int. Cl.
*A61B 34/32* (2016.01)
*A61B 34/00* (2016.01)
(Continued)

(52) U.S. Cl.
CPC .............. *A61B 34/32* (2016.02); *A61B 34/20* (2016.02); *A61B 34/37* (2016.02); *A61B 34/77* (2016.02);
(Continued)

(58) Field of Classification Search
None
See application file for complete search history.

(56) References Cited

U.S. PATENT DOCUMENTS

| | | | |
|---|---|---|---|
| 5,855,553 A | 1/1999 | Tajima et al. | |
| 2005/0177054 A1 | 8/2005 | Yi et al. | |

(Continued)

FOREIGN PATENT DOCUMENTS

| | | |
|---|---|---|
| CN | 110573105 A | 12/2019 |
| DE | 69623674 T2 | 5/2003 |
| EP | 2600813 B1 | 1/2021 |

OTHER PUBLICATIONS

International Search Report in PCT/FR2022/050456, mailed Jun. 24, 2022, 4 pages.
(Continued)

*Primary Examiner* — Carl H Layno
*Assistant Examiner* — Bryan Mcallister Lee
(74) *Attorney, Agent, or Firm* — ArentFox Schiff LLP

(57) ABSTRACT
The invention relates to a medical robot for assisting a practitioner during a medical intervention on a relevant anatomical part of a patient. The medical robot comprises a robotic arm equipped, at one end, with a tool guide intended to guide a medical instrument. The medical robot also comprises a control unit configured to control the movement of the robotic arm. The tool guide is coupled to a force sensor. When the medical robot is used in a "cooperative manual control" mode, the control unit is configured to determine, using the force sensor, a force applied by the practitioner to the tool guide and to calculate a speed of movement of the tool guide on the basis of a gain factor applied to the determined force. Advantageously, the value of the gain factor is variable and is calculated on the basis of the determined force.

12 Claims, 7 Drawing Sheets

(51) Int. Cl.

| | |
|---|---|
| *A61B 34/20* | (2016.01) |
| *A61B 34/30* | (2016.01) |
| *A61B 34/37* | (2016.01) |
| *A61B 90/00* | (2016.01) |

(52) U.S. Cl.
CPC ........ *A61B 90/39* (2016.02); *A61B 2034/302* (2016.02); *A61B 2090/3937* (2016.02)

(56) References Cited

U.S. PATENT DOCUMENTS

| | | |
|---|---|---|
| 2014/0052150 A1 | 2/2014 | Taylor et al. |
| 2018/0008358 A1 | 1/2018 | Kostrzewski et al. |
| 2018/0289432 A1 | 10/2018 | Kostrzewski et al. |
| 2019/0090966 A1* | 3/2019 | Kang ..................... A61B 34/30 |

OTHER PUBLICATIONS

Written Opinion in PCT/FR2022/050456, mailed Jun. 24, 2022, 6 pages.

* cited by examiner

COLLABORATIVE MEDICAL ROBOT FOR SECURE INSTRUMENT GUIDANCE

CROSS-REFERENCE TO RELATED APPLICATIONS

This application is a National Phase of PCT/FR2022/050456, filed on Mar. 14, 2022, which claims priority to FR Patent Application No. FR2102647, filed on Mar. 17, 2021, the disclosures of which are hereby incorporated by reference in their entireties.

FIELD OF THE INVENTION

The present invention belongs to the field of robotised devices to assist a practitioner during a medical or surgical procedure. More particularly, the invention concerns a medical robot comprising a robotised arm equipped with a tool guide to guide and release a medical instrument during a mini-invasive or percutaneous medical procedure.

PRIOR ART

Medical procedures which are carried out by mini-invasive or percutaneous means may require the insertion by a practitioner of one or a plurality of medical instruments (for example needle, a probe, a catheter, etc.) into the body of a patient down to a given depth in order to reach a target anatomical area (for example a tumour in the liver, a lung, a kidney, or a bone).

When the movement of insertion of the medical instrument is carried out entirely by the practitioner, the result of the procedure is highly dependent on the skill of the practitioner. The precision of the movement can be improved thanks to the assistance of remote-controlled medical robots. In this case also, the success of the procedure is still partly dependent on the skill of the practitioner, and it may be necessary to acquire medical images of the patient continuously, which involves subjecting the patient to large doses of radiation.

In order to improve further the precision of the movement of insertion and to limit the doses of radiation on the patient, it is possible to use robotised arms which are controlled automatically. The robotised arm can be equipped with a tool guide to guide a medical instrument. The practitioner indicates for example on a pre-intervention medical image a trajectory which the medical instrument must follow in order to reach a target area of the relevant part of the anatomy of the patient, and the robotised arm is displaced automatically into a position such that the tool guide makes it possible to guide the medical instrument according to the trajectory planned.

It is advantageous for the practitioner to be able to displace the robotised arm manually in order to bring the tool guide towards the relevant part of the anatomy of the patient, or to release the tool guide after an (optionally partial) insertion of the medical instrument. When the robotised arm is displaced manually by the practitioner, and when the tool guide is relatively distant from the relevant part of the anatomy of the patient, the movement of the robotised arm must be fluid and reactive. On the other hand, when the tool guide is relatively close to the relevant part of the anatomy of the patient, the movement of the robotised arm must be controlled with precision and at a low speed in order to reach the position of insertion of the medical instrument with exactitude, and without risking injuring the patient with the medical instrument or the tool guide. Also, it is necessary to avoid jerky movements of the robotised arm caused by trembling by the practitioner.

For this purpose, it can be envisaged to carry out a frequency study of the forces exerted by the practitioner by means of an accelerometer, in order to determine whether trembling is present or not. However, a solution of this type is relatively complex to implement, and requires integration of an additional sensor (the accelerometer) in the medical robot.

It is also necessary to undertake measures to ensure that the patient cannot be injured by the medical instrument during the procedure, for example if the patient makes an unexpected movement when the robotised arm is guiding the medical instrument during its insertion into the body of the patient. The medical instrument is generally inserted while the patient is apnoeic. It is therefore also necessary to ensure that the patient cannot be injured by the medical instrument in the event of the respiratory movements resuming before the medical instrument has been released from the tool guide.

SUMMARY OF THE INVENTION

The objective of the present invention is to eliminate some or all of the disadvantages of the prior art, in particular those summarised above.

For this purpose, and according to a first aspect, the present invention proposes a medical robot to assist a practitioner during a medical procedure on a relevant part of the anatomy of a patient. The medical robot comprises a robotised arm comprising at a distal end a tool guide which is designed to guide a medical instrument. The medical robot also comprises a control unit which is configured to control the displacement of the robotised arm. The tool guide is coupled to a force sensor. When the medical robot is used in a "cooperative manual control" mode, the control unit is configured to determine, by means of the force sensor, a force exerted by the practitioner on the tool guide, and to calculate a speed of displacement of the tool guide according to a gain factor applied to the force thus determined. Advantageously, the value of said gain factor is variable, and is calculated according to the force which is exerted by the practitioner on the tool guide. The control unit is configured to control the displacement of the robotised arm according to the speed thus calculated.

Thus, the practitioner displaces the robotised arm by exerting a force with his hand on the tool guide which is secured on the end of the robotised arm. The force sensor allows the control unit to control the speed of displacement of the robotised arm according to the force exerted by the practitioner. In fact, the speed of displacement of the tool guide is calculated by applying a gain factor to the force exerted by the practitioner on the tool guide. The force which is exerted by the practitioner on the tool guide is for example determined by the control unit on the basis of the forces and moments measured by the force sensor by a series of operations which can include filtering, noise reduction, compensation for the weight of the tool guide, transposition to a reference point of the tool guide, etc. The greater the force exerted by the practitioner on the tool guide is, the greater the speed of displacement of the tool guide calculated by the control unit is. Thus, when the tool guide is relatively far from the patient, and the practitioner exerts a significant force on the tool guide, the robotised arm is displaced rapidly, fluidly, and reactively. On the other hand, when the practitioner exerts a slight force on the tool guide because the tool guide is close to the body of the patient, the robotised arm is displaced at a low speed in order to guarantee precision and safety.

In addition, and as will be explained hereinafter, the fact that the gain factor varies according to the force exerted by the practitioner on the tool guide makes it possible to avoid jerking in the displacement of the robotised arm generated by trembling by the practitioner (with the trembling corresponding to a low-amplitude force varying with a high frequency).

For example, the gain factor varies linearly with the force exerted by the practitioner on the tool guide, when this force varies between a minimal value $F_{min}$ and a maximal value $F_{max}$.

In particular embodiments, the invention can also comprise one or more of the following characteristics, taken in isolation or according to all the combinations which are technically possible.

In particular embodiments, the gain factor corresponds to a proportional parameter of a Proportional Integral Derivative corrector implemented by the control unit.

By means of a control loop, the control unit calculates a speed of displacement of the tool guide which is intended to cancel out the force exerted by the practitioner. For this purpose, a PID corrector can be used. PID is the acronym for Proportional Integral, Derivative. It is a closed-loop control system which is commonly used in industry. In fact, the invention is based on the hypothesis that movements generated by a low-amplitude force exerted by the practitioner will comprise trembling. The solution proposed thus does not require frequent analysis in order to detect trembling. Adopting this hypothesis makes it possible to simplify the problem and to use a PID corrector.

In particular embodiments, the control unit is also configured to prevent the displacement of the tool guide in at least one direction.

The term "direction" corresponds to a degree of freedom of the tool guide in a three-dimensional reference system (x, y, z) in which it is incorporated. This direction can in particular be a translation along each of the axes x, y or z, or a rotation around each of these axes.

Arrangements of this type make it possible to control the displacement of the robotised arm, in order for example to prevent the tool guide from colliding with the medical instrument when the robotised arm is released after the partial or total insertion of the medical instrument into the body of the patient, and after the release of the medical instrument from the tool guide.

In particular embodiments, the control unit is also configured to limit the displacement of the tool guide in a single direction, corresponding for example to a main axis of the tool guide.

Arrangements of this type make it possible to control the displacement of the robotised arm, for example in order to bring the robotised arm into a position corresponding to the position in which the medical instrument has been inserted.

In particular embodiments, the value of the gain factor is defined thus:

$$G(f) = K \times \left(1 + \frac{|f| - F_{min}}{F_{max} - F_{min}}\right) \text{ if } F_{min} \le |f| \le F_{max} \quad \text{[Math. 1]}$$

where G(f) is the gain factor; K is a constant; |f| is the force exerted by the practitioner on the tool guide, determined by the control unit by means of the force sensor; $F_{min}$ and $F_{max}$ correspond respectively to a minimal value and a maximal value for the force exerted by the practitioner. |f|, $F_{min}$ and $F_{max}$ correspond to standards of a force (intensities of the force measured in Newtons). Hereinafter in the description, and unless otherwise indicated, when reference is made to the "force" exerted by the practitioner or by the medical instrument, somewhat imprecisely this means "the intensity of the force". By way of example, $F_{min}$ is equal to 2 N and $F_{max}$ is equal to 60 N.

In particular embodiments, the control unit is configured to calculate the speed of displacement of the tool guide also according to a distance between a current position of the tool guide and a target position which the tool guide must reach.

In particular, arrangements of this type make it possible to limit further the speed of approach of the tool guide as the tool guide approaches its target position, in order to increase the precision and safety when the medical instrument is close to the relevant part of the anatomy of the patient.

In particular embodiments, the robotised arm is an articulated arm which has at least six degrees of freedom.

The use of at least six degrees of freedom at the robotised arm makes it possible to ensure that any position in space can be reached by the tool guide. Furthermore, if the medical instrument has axial symmetry (for example if the medical instrument is a needle), then five degrees of freedom are sufficient, since it is not necessary to carry out rotation around the axis of symmetry of the medical instrument. This additional degree of freedom makes it possible to be in a situation of redundancy, and to have infinite possible configurations of the robotised arm for a given position. This provides a certain amount of flexibility, since the practitioner can then for example select the optimal configuration of the robotised arm according to constraints inherent in the procedure room (space available for the medical staff, the presence of obstacles, visibility of the tool guide by any navigation system, etc.).

In particular embodiments, when the medical robot is being used in a "medical instrument insertion" mode, the control unit is configured to prevent any displacement of the tool guide, and, by means of the force sensor, to determine a force exerted on the medical instrument. The tool guide comprises means to release the medical instrument automatically at a command from the control unit. The control unit is configured to command the tool guide to release the medical instrument when the force exerted on the medical instrument is greater than a predetermined threshold value, or when a variation of the force exerted on the medical instrument over a given period of time is greater than a predetermined threshold value.

Arrangements of this type make it possible to release the medical instrument immediately, during the phase of insertion of the medical instrument (i.e. when the medical instrument is retained in the tool guide in order to guide the insertion thereof into the body of the patient), for example if the patient exerts an unexpected force on the medical instrument as a result of respiratory movements, whereas the patient should be apnoeic.

In particular embodiments, the tool guide comprises at least one marker which can be detected by a navigation system, and the control unit is configured to:

receive from said navigation system a first piece of information relating to a position of the tool guide in a reference of the navigation system;

receive from said navigation system a second piece of information relating to a target position, in the reference of the navigation system, which the tool guide must reach;

determine the target position, in a reference of the medical robot, by means of the second piece of information;

displace the robotised arm, in an "automatic control" mode, without the intervention of the practitioner, in order for the tool guide to reach the target position.

Arrangements of this type make it possible to displace the robotised arm automatically and precisely to bring the tool guide into a target position in which the medical instrument can be inserted into the body of the patient, in order to carry out the surgical procedure.

In particular, the target position of the tool guide can be determined according to a trajectory which the medical instrument must follow, planned on a pre-intervention medical image. For this purpose, in particular embodiments, the second piece of information corresponds to a position, in the reference of the navigation system, of a patient reference which is intended to be positioned on the patient in the vicinity of the relevant part of the anatomy. The patient reference comprises at least one marker which can be detected by the navigation system, and at least one radio-opaque marker. The trajectory is defined relative to the position of the patient reference by means of a pre-intervention medical image on which there can be seen the relevant part of the anatomy of the patient and the radio-opaque marker of the patient reference. The control unit is configured to determine the target position of the tool guide from the position of the patient reference and from the planned trajectory.

In particular embodiments, the control unit is configured to:

store as the reference position a position at a first instant of the tool guide relative to the position of the patient reference;

determine whether a difference between a position at the second instant of the tool guide and the reference position is lower than a predetermined threshold.

Arrangements of this type are particularly advantageous in the situation where the robotised arm must be released after a partial insertion of the medical instrument, for example in order to permit the acquisition of a medical image in order to verify whether the medical instrument is suitably inserted, and the robotised arm must then be brought to the initial position in which the medical instrument was inserted, for example in order to finalise the insertion of the medical instrument.

In particular embodiments, the tool guide comprises means for releasing the medical instrument automatically at the command of the control unit. The control unit is configured to command the tool guide to release the medical instrument when the control unit receives information from the navigation system indicating an unexpected displacement of the patient reference.

It is thus possible to avoid injuring the patient with the medical instrument when the patient makes an unexpected movement during the insertion of the medical instrument into the body of the patient.

PRESENTATION OF THE FIGURES

The invention will be better understood by reading the following description, provided by way of non-limiting example, and produced with reference to FIGS. 1 to 9, which represent the following:

Figure 8:
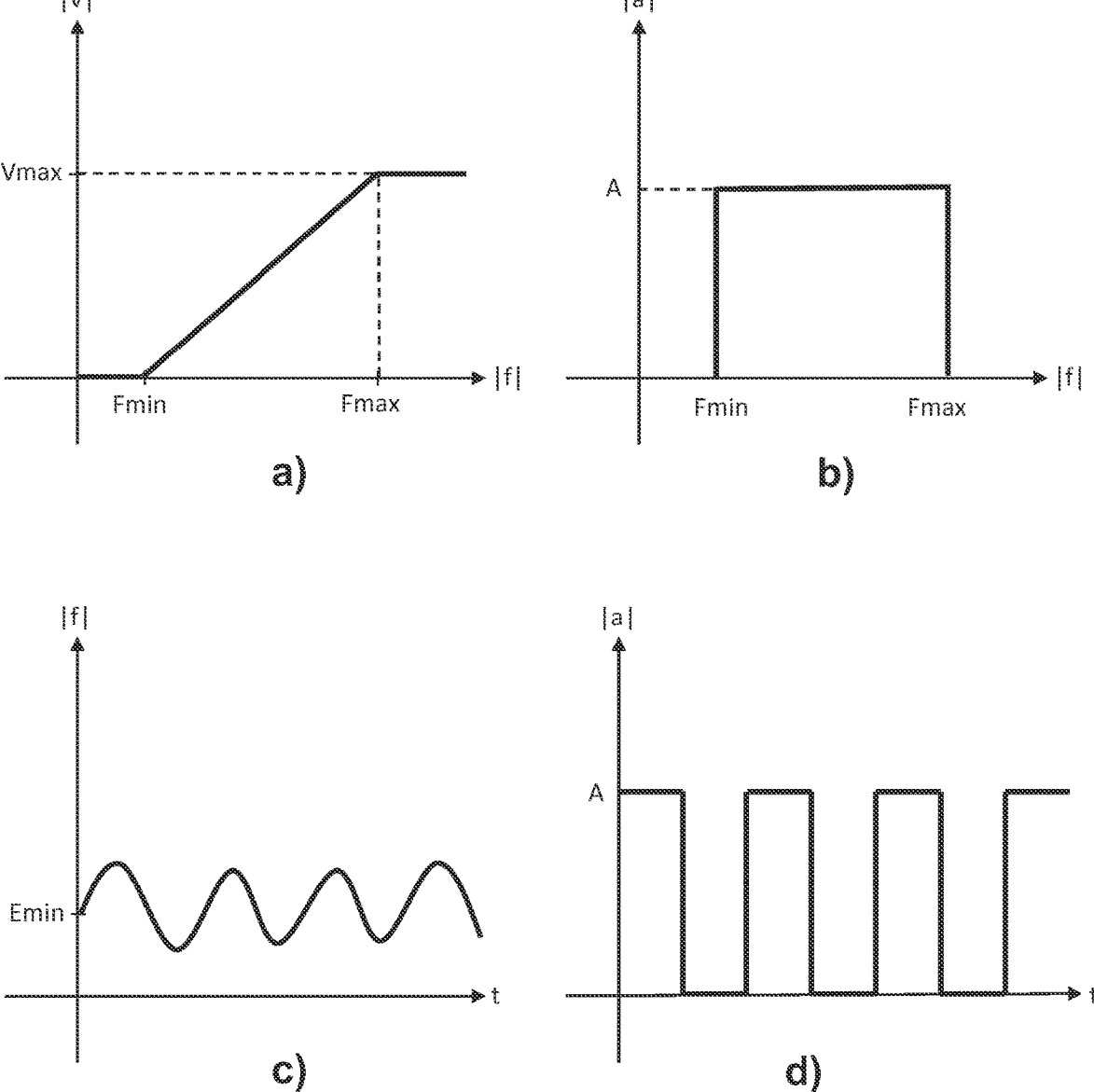
Figure 9:
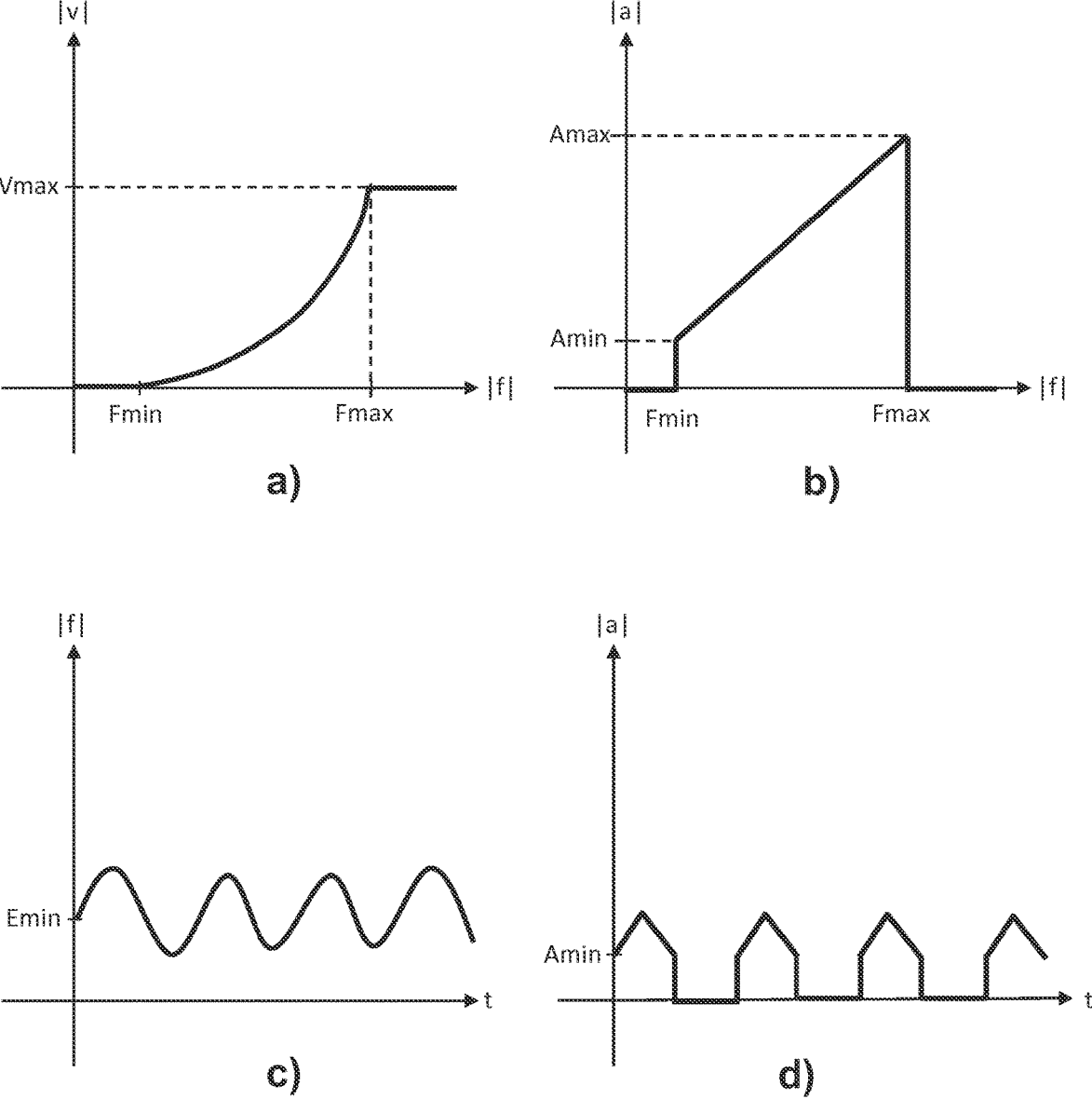

FIG. 8 consists of graphs representing in particular the speed and the acceleration to which the tool guide is subjected according to the force exerted by the practitioner on the tool guide, in a case where the speed is defined according to a constant gain factor applied to the force exerted;

FIG. 9 consists of graphs similar to those represented in FIG. 8, in a case where the speed is defined according to a variable gain factor applied to the force exerted, with the gain factor varying according to the force exerted.

In these figures, references which are identical from one figure to another designate identical or analogous elements. For reasons of clarity, the elements represented are not necessarily to the same scale, unless otherwise stated.

DETAILED DESCRIPTION OF AN EMBODIMENT OF THE INVENTION

Figure 1:
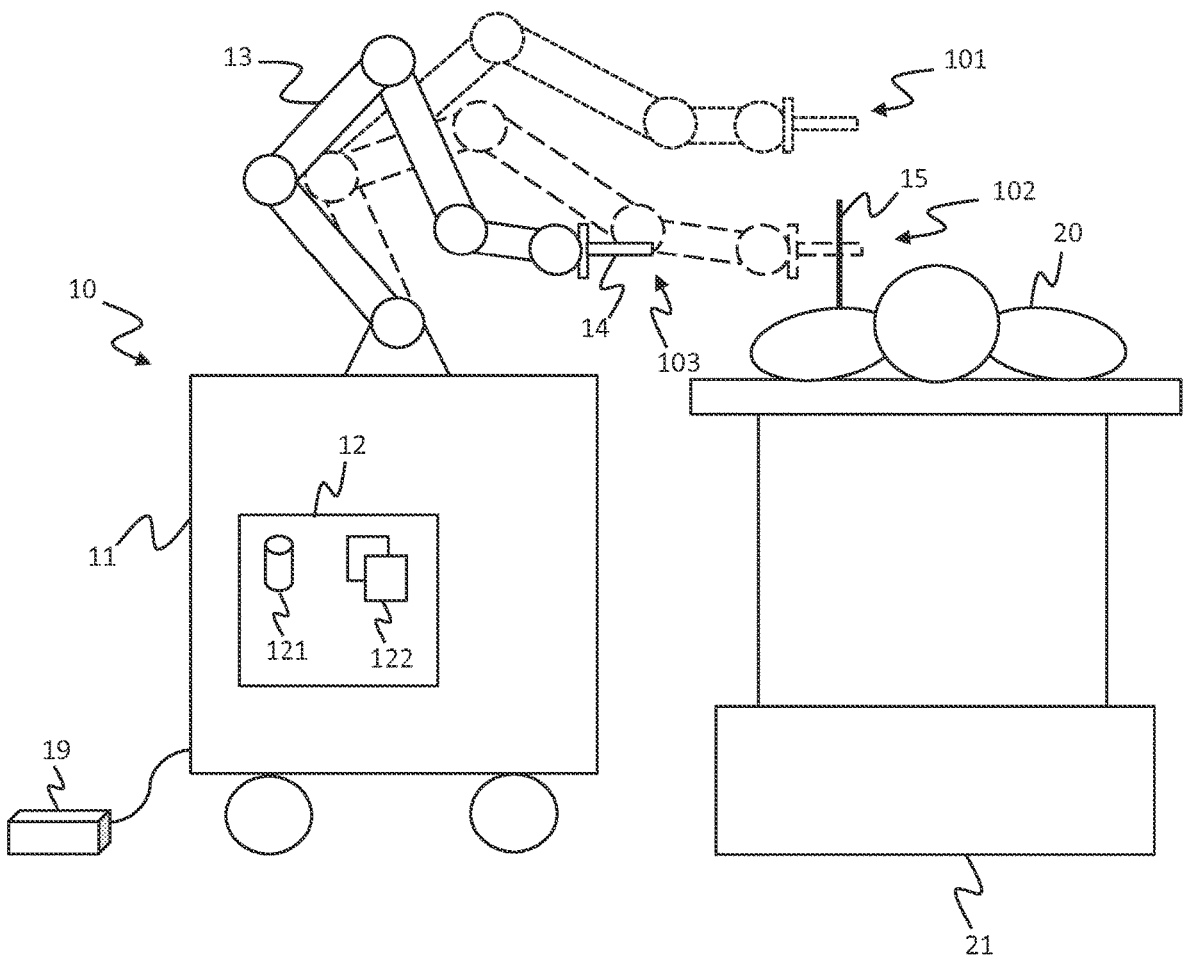
FIG. 1 is a schematic representation of a medical robot according to the invention, to assist a practitioner during a medical procedure on a relevant part of the anatomy of a patient.

FIG. 1 represents schematically a medical robot 10 according to the invention. The medical robot 10 is used to assist a practitioner during a medical procedure on a relevant part of the anatomy of a patient 20 positioned on a procedure table 21.

By way of non-limiting example, the case is used of a medical procedure carried out by mini-invasive or percutaneous means. This type of procedure generally requires insertion by the practitioner of one or more medical instruments (for example needle, a probe, a catheter, etc.) into the body of the patient, down to a given depth, in order to reach a target anatomical area in the relevant part of the anatomy (for example a tumour in the liver, a lung, a kidney, etc.).

The medical robot 10 comprises a base 11. In the example considered, the base 11 of the medical robot 10 is equipped with motorised wheels, which allows the medical robot 10 to be displaced in different directions by movements of translation and/or rotation.

The medical robot 10 also comprises an articulated robotised arm 13, one end of which is connected to the base 11. At the other end of the robotised arm 13, there is secured a guide tool 14 which is designed to guide a medical instrument 15, such as, for example, a needle, a probe, a catheter, an electrode, etc. The medical robot 10 can thus be used to help a practitioner to position, retain, or guide the medical instrument 15 during the medical procedure. The medical robot 10 thus plays the part of a third hand for the practitioner.

Figure 2:
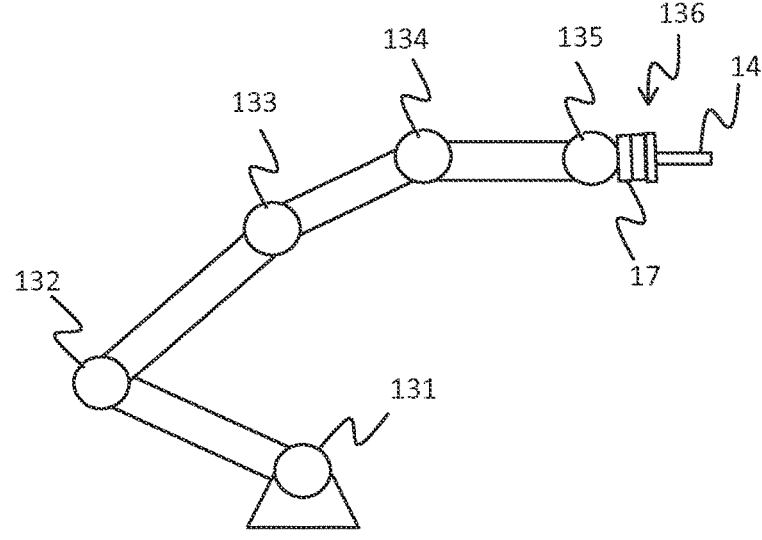
FIG. 2 is a schematic representation of the robotised arm of the medical robot.

In the example considered and illustrated in FIG. 2, the robotised arm 13 comprises six swivel articulations 131 to 136, providing six degrees of freedom, making it possible to position and/or displace the medical instrument 15 into any position of a three-dimensional space. Advantageously, the articulations 131 to 135 of the robotised arm 13 are not aligned, and have offsetting relative to one another, which permits a larger number of possible configurations of the robotised arm 13. Each articulation comprises at least one encoder making it possible to determine the angular position thereof in real-time. A configuration of the robotised arm 13 thus corresponds to a series of values of parameters taken by the articulations 131 to 136 (for example the value of an angle of rotation for each articulation). The swivel articulation 136 corresponds to a rotation around the main axis of the tool guide 14. It should be noted that it is however not necessary to carry out a rotation around the axis of symmetry of the medical instrument (in fact five degrees of freedom are sufficient to guide and release a medical instrument). This additional degree of freedom makes it possible to be in a situation of redundancy, and to have infinite possible configurations of the robotised arm 13 for a given position of the tool guide 14. This situation of redundancy is particularly advantageous for adapting to constraints associated with the position of the patient or the configuration of the procedure room.

Figure 3:
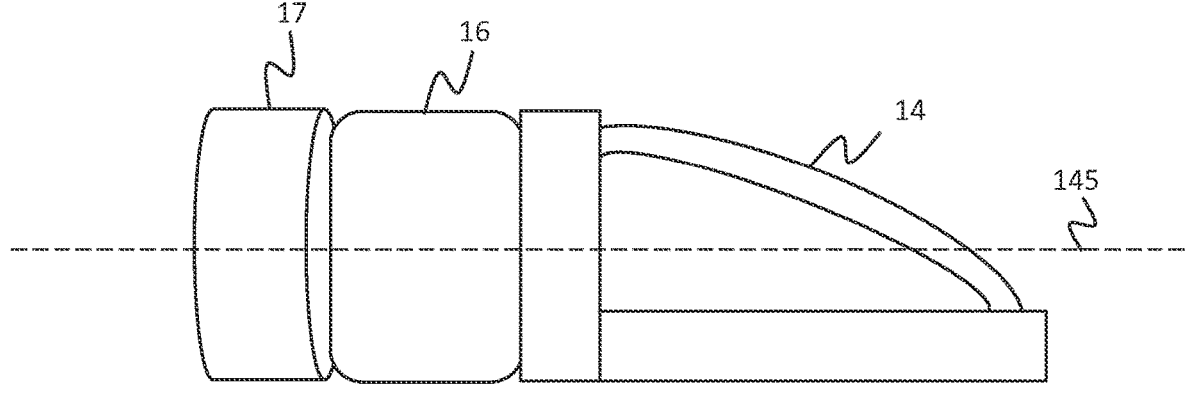
FIG. 3 is a schematic representation of the tool guide which is designed to be secured on the end of the robotised arm.

As illustrated in FIG. 3, the tool guide 14 is secured on the robotised arm 13 by means of a flange 17. The tool guide comprises a main axis 145 which is represented by a broken line in FIG. 3. The tool guide 14 is coupled to a force sensor 16, in order to allow the control unit 12 to determine a force exerted on the tool guide 14. This force can in particular be exerted by the practitioner when he displaces the robotised arm 13 manually. This force can also correspond to a force exerted on the tool guide 14 via the medical instrument 15 by the body of the patient (for example as the result of an accidental movement of the patient during the insertion of the medical instrument).

It should be noted that the force sensor makes it possible to measure a total force corresponding to the resultant of the forces and moments to which the force sensor 16 is subjected (including not only the force exerted by the practitioner, but also the weight of the tool guide 14, the weight of the medical instrument 15, etc.). The control unit is configured to determine the force exerted by the practitioner on the tool guide 14 according to the resultant of the forces and moments to which the force sensor 16 is subjected. For this purpose, it is necessary for example to subtract from the total force the force corresponding to the weight of the tool guide 14, the force corresponding to the weight of the medical instrument 15, if the instrument is being retained by the tool guide 14, a torque caused by the difference between the point of measurement and the centre of mass of the tool guide, and/or any compensation associated with the measurement noises. It can also be envisaged to carry out filtering on the measurements made by the force sensor 16.

Figure 4:
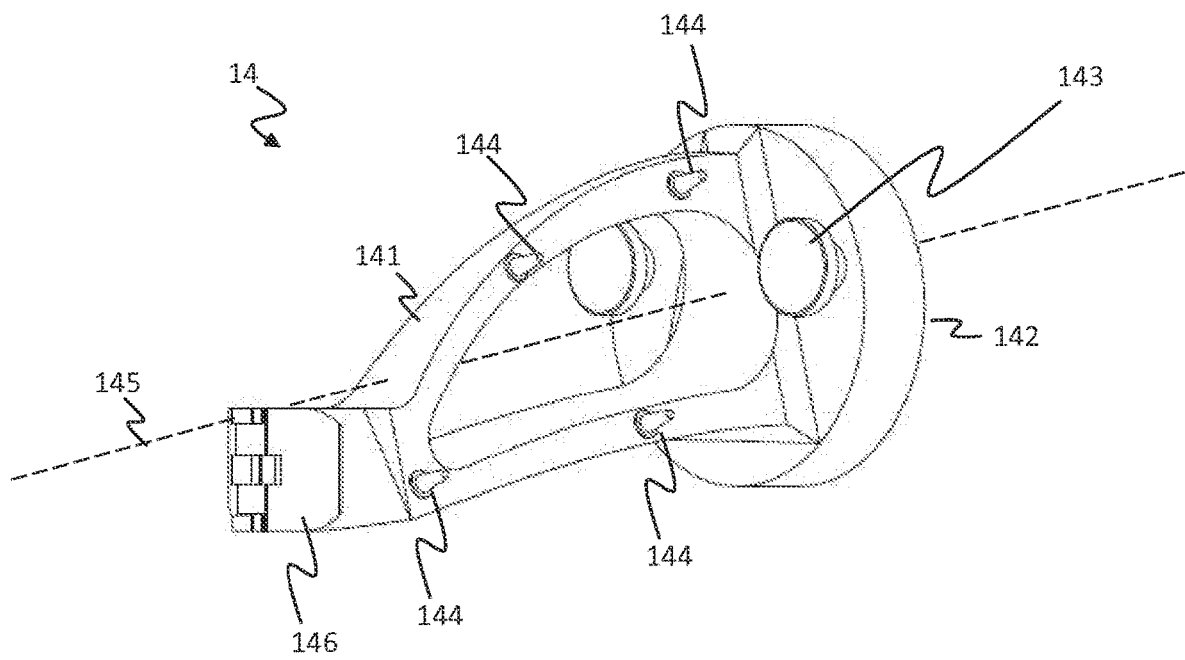
FIG. 4 is a representation of the tool guide, showing a device for retention of the medical instrument on the end of the tool guide.
Figure 5:
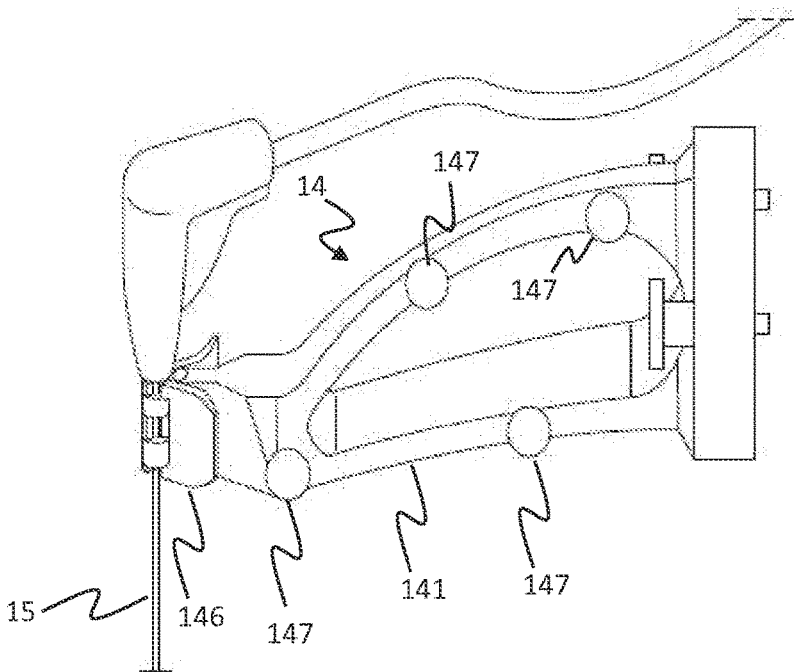
FIG. 5 is a representation of the tool guide showing the positioning of the medical instrument on the tool guide, as well as markers which can be detected by a navigation system.

As illustrated in FIGS. 4 and 5, the tool guide 14 comprises a body 141 with a base 142 which is designed to be secured on the flange 17 by means of a screw 143, as well as a retention system 146 comprising two parts which are movable relative to one another. The retention system 146 is designed to retain the medical instrument 15 at the end of the body 141 of the tool guide 14 opposite the base 142. The two movable parts of the retention system 146 can be driven by a drive system such as a gear, a cam, a screw with inverted threads and/or a linear actuator, in order to block or release the medical instrument 15. The linear actuator can be reversible (the retention system 146 of the tool guide 14 can then be opened manually or automatically at a command from the control unit 12), or non-reversible (the retention system 146 of the tool guide 14 can be opened only automatically at a command from the control unit). The tool guide 14 makes it possible for example to guide medical instruments with different diameters. For example, a guide of this type makes it possible to guide medical instruments, the diameter of which is between 11 and 21 gauges. The gauge is a measurement unit which is commonly used to define the outer diameter of a medical instrument such as a needle, a probe or a catheter (11 gauges correspond to an outer diameter of 2.946 mm; 21 gauges correspond to an outer diameter of 0.812 mm).

As illustrated in FIG. 1, the medical robot 10 comprises a control unit 12 which is configured to control the displacement of the robotised arm 13. The control unit 12 comprises for example one or more processors 122 and a memory 121 (magnetic hard disc, electronic memory, optical disc, etc), in which a computer programme product is stored in the form of a set of programme code instructions to be executed in order to implement the different steps of a method for positioning of the robotised arm 13.

Figure 7:
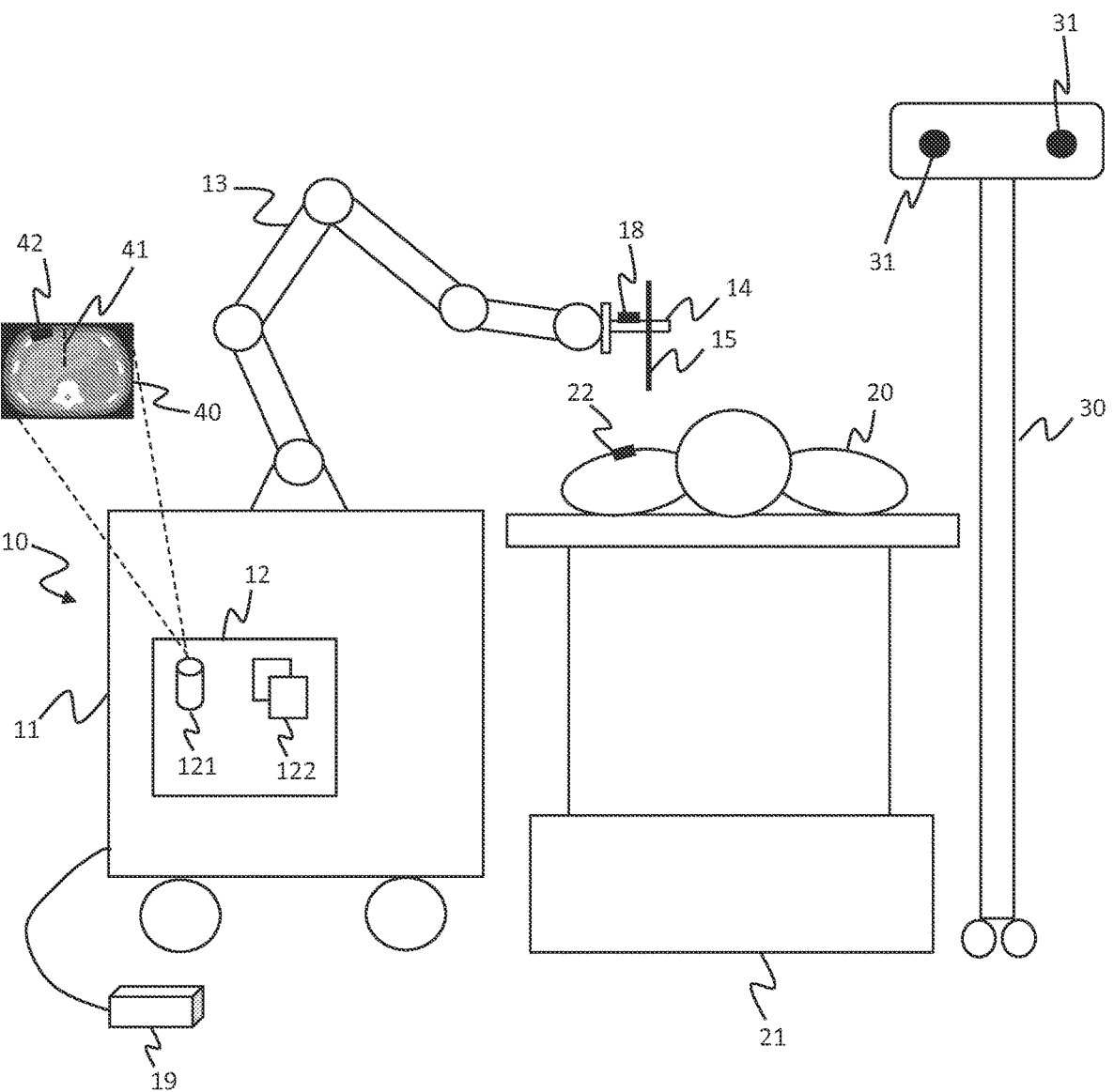
FIG. 7 is an illustration of the cooperation between the medical robot according to the invention and a navigation device.

As illustrated in FIG. 7, a navigation system 30 can be used to provide the control unit 12 of the medical robot 10 with information relating to a current position of the tool guide 14 and to a target position which the tool guide must reach. The current position and the target position provided are for example initially defined in a reference of the navigation system 30, then transformed into positions in a reference of the medical robot 10 by the control unit 12. The control unit can then be configured to displace the robotised arm 13 automatically (in a so-called "automatic control" mode, without intervention by the practitioner), such that it reaches the target position. The navigation system 30 and the control unit 12 of the medical robot 10 can exchange data via (wired or wireless) communications means.

In the present application, the term "position" corresponds to the combination of the position and the orientation of an object in a given reference which is generally a three-dimensional coordinates system. The term "pose" is used in the Anglo-Saxon literature to represent this combination of the position and the orientation of an object in space.

In the example considered, the navigation system 30 is an optical navigation system. The navigation system 30 comprises at least two optical sensors 31 corresponding for example to two sensors of a stereoscopic camera operating in the field of infrared radiation or in the field of visible light.

As illustrated in FIGS. 4 and 5, the tool guide 14 comprises studs 144 which are designed to receive optical markers 147. Advantageously, the tool guide 14 comprises at least three optical markers 147 such that the position of the tool guide 14 can be determined in the three spatial dimensions of the reference system of the navigation system 30. The respective positions of the optical markers 147 of the tool guide relative to one another are known a priori by the navigation device 30 and/or by the control unit 12. Advantageously, the geometric form of each optical marker 147 can also be known a priori. In the example illustrated in FIG. 5, the optical markers 147 have a spherical form.

The use of at least three optical markers 147 makes it possible to define a plane, and thus a direct orthonormal three-dimensional reference with an axis z which is normal to the plane, and axes x and y on the plane, such that the reference is direct. This therefore makes it possible to determine the position and the orientation of the reference formed from optical markers 147 which represent the tool guide 14. The three axes x, y and z make it possible to define six degrees of freedom, i.e. translation along each of the axes x, y or z, and rotation around each of these axes.

The optical markers 147 can be passive or active. Passive optical markers reflect optical radiation emitted by another element, such as, for example, the navigation system 30. Passive optical markers can correspond for example to reflective spheres which can be detected by an infrared stereoscopic camera (which is what is used for example in the Polaris® navigation systems which are produced by the company Northern Digital Inc.), or to black-and-white patterns which are visible by a stereoscopic camera (which is what is used for example in the MicronTracker® navigation system by the company ClaroNav). Active optical markers themselves emit optical radiation, for example infrared radiation, which can be detected by the navigation system 30.

As illustrated in FIG. 7, the assembly of the markers 147 which are present on the tool guide 14 corresponds to a robot reference 18.

It should be noted however that a single optical marker with a characteristic geometric form in three dimensions could be used in the place of the assembly of the spherical optical markers 147.

Figure 6:
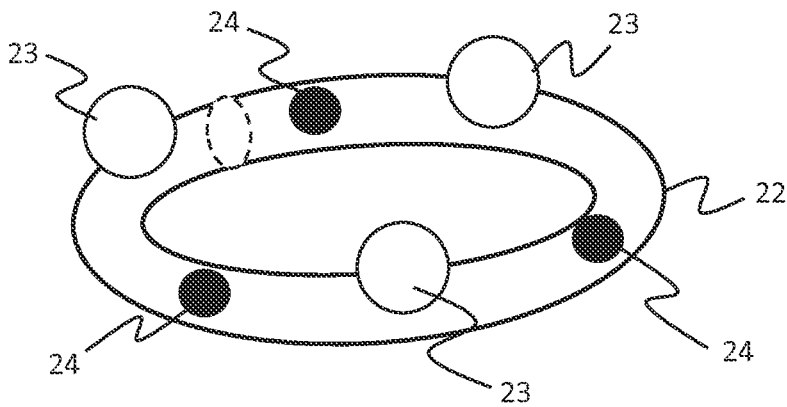
FIG. 6 is a schematic representation of a patient reference which is designed to be positioned on the patient in the vicinity of the relevant part of the anatomy.

A patient reference 22 is positioned on the patient 20 in the vicinity of the relevant part of the anatomy. FIG. 6 represents schematically the patient reference 22. The patient reference 22 comprises at least three optical markers 23, such that the position of the patient reference 22 can be determined in the three spatial dimensions of the reference system of the navigation system 30. The respective positions of the optical markers 23 of the patient reference 22 relative to one another are known a priori by the navigation system 30 and/or by the control unit 12. Advantageously, the geometric form of each optical marker 23 can also be known a priori. In the example illustrated in FIG. 6, the patient reference 22 comprises three optical markers 23 with a spherical form. The spherical form makes it possible to optimise the reflection of the optical radiation. The description previously given for the active or passive type of optical markers 147 of the tool guide 14 also applies to the optical markers 23 of the patient reference 22. In this case also, it could be envisaged to use a single optical marker with a characteristic geometric form in three dimensions in the place of the three spherical optical markers 23.

Hereinafter in the description, it is considered by way of example which is in no way limiting that the optical sensors 31 of the navigation system 30 and the different optical markers 147, 23 are designed to operate with optical radiation of the infrared type. It can also be considered that the optical markers 147, 23 are passive markers. The optical sensors 31 are configured to emit infrared radiation. This infrared radiation is reflected by the different optical markers 147, 23 towards the optical sensors 31. The optical sensors 31 are configured to receive this reflected infrared radiation. The navigation system 30 can then determine the distance between an optical marker 147, 23 and an optical sensor 31 by measuring the time taken by an infrared ray to complete the outward and return distance between said optical sensor 31 and said optical marker 147, 23. By knowing the distance between each optical marker 147, 23 and each optical sensor 31, and by knowing a priori the arrangement of the optical markers 147, 23 relative to one another on the tool guide 14 and on the patient reference 22, it is possible to determine the position of the tool guide 14 and of the patient reference 22 in the reference system of the navigation system 30.

The target position which the tool guide 14 must reach can be defined in particular from the patient reference 22 position. For this purpose, and as illustrated in FIG. 6, the patient reference 22 also comprises radio-opaque markers 24, which are visible on a medical image acquired by a medical imagery device (for example by tomodensitometry, by magnetic resonance, by ultrasound, by tomography, by emission of positions, etc.). The respective positions of the radio-opaque markers 24 relative to one another are known a priori by the navigation device 30 and/or by the control unit 12. Advantageously, the geometric form of the radio-opaque markers 24 can also be known a priori. Preferably, the patient reference 22 comprises at least three radio-opaque markers 24. The radio-opaque markers 24 can for example be ceramic balls. It should however be noted that a single radio-opaque marker with a characteristic geometric form in three dimensions could be used in the place of the three spherical radio-opaque markers 24.

It is thus possible to plan the medical procedure from a pre-intervention medical image 40 of the patient provided with the patient reference 22. This pre-intervention medical image 40 is stored in the memory 121 of the control unit 12. It is thus possible, from the pre-intervention medical image 40, to define the target position which the tool guide 14 must adopt in order to guide the medical instrument 15, to carry out the medical procedure. The planning comprises determination, on the pre-intervention image 40, of the trajectory 41 which must be followed by the medical instrument 15 (for example a needle), between an entry point at the skin of the patient 20 and a target point (for example a tumour) in the relevant part of the anatomy of the patient 20. The reference 42 in FIG. 7 represents the assembly of the radio-opaque markers 24 of the patient reference 22, which markers can be seen on the pre-intervention image 40 (this therefore represents the image of the patient reference 22 on the pre-intervention image 40). The target position of the tool guide 14 which makes it possible to follow the trajectory 41 can thus be defined relative to the position of patient reference 22.

It should be noted that the determination of the trajectory can also be carried out on a pre-operative image acquired several days before the procedure (which image is acquired without the patient being provided with the patient reference). The pre-operative image can then be reset with the pre-intervention image 40 on which the patient reference can be seen, in order to obtain a relative position of the patient reference 22 in relation to the trajectory.

In the example concerned, the navigation system 30 is configured to provide the control unit 12 of the medical robot 10 with the current position of the tool guide 14 in the reference of the navigation system 30. However, the control unit 12 of the medical robot 10 knows the current position of the tool guide 14 in the reference system of the medical robot 10 (via the encoders of the articulations 131 to 136). The control unit 12 can thus determine the transformation to put into effect in order to define a position in the reference system of the medical robot 10 from a position in the reference system of the navigation device 30. The navigation system 30 is also configured to provide the control unit 12 of the medical robot with the patient reference 22 position in the reference of the navigation system 30. The control unit 10 can thus define the position of the patient reference 22 in the reference system of the medical robot 10. However, thanks to the pre-intervention image 40, the control unit 12 of the medical robot 10 knows the position of the target position which the tool guide 14 must reach relative to the patient reference 22 position. The control unit 12 can thus determine the target position which the tool guide 14 must reach from information provided by the navigation system 30. The control unit 12 can thus be configured (in a so-called "automatic control" mode, without the intervention of the practitioner) to displace the robotised arm 13 automatically such that it reaches the target position.

The displacements of the robotised arm 13 are for example dependent on the selection of a control mode on a user interface of the medical robot 10, and on activation of the mode selected by a control pedal 19.

A so-called "cooperative manual control" mode corresponds to a mode in which the practitioner can himself displace the robotised arm 13 manually, however with control of the displacement of the robotised arm 13 by the control unit 12 (in order to limit the speed and/or the possible directions of displacement of the robotised arm 13).

A so-called "automatic control" mode corresponds to a mode in which the robotised arm 13 is completely controlled by the control unit 12. The robotised arm 13 is thus displaced automatically, without the intervention of the practitioner.

A plurality of "cooperative manual control" modes exist.

A so-called "approach cooperative manual control" mode corresponds for example to a mode in which the practitioner displaces the robotised arm 13 in order to bring the guide tool 14 towards a position of approach 101 which is relatively close to the relevant part of the anatomy of the patient, and in order for the robotised arm 13 to enter the field of vision of the navigation system 30. In this mode, it is advantageous to control the speed of displacement of the robotised arm 13 according to the force exerted by the practitioner on the robotised arm 13. In this mode, the displacement of the robotised arm 13 is generally permitted in all directions.

The robotised arm can then be displaced automatically (in the "automatic control" mode) from the position of approach 101 to the position of insertion 102. The position of insertion 102 corresponds to the target position in which the tool guide 14 must be positioned in order for the medical instrument 15 to be able to follow the planned trajectory.

A so-called "release cooperative manual control" mode corresponds for example to a mode in which, after partial insertion of the medical instrument 15 into the body of the patient 20, the medical instrument 15 can be released from the retention device 146 of the tool guide 14, and the robotised arm 13 can be released manually by the practitioner from the position of insertion 102 towards a released position 103. Arrangements of this type make it possible to move the patient 20 in order to create a control medical image after the partial insertion of the medical instrument 15 (for example to check that the trajectory followed by the medical instrument corresponds to the planned trajectory). In this mode, it can be advantageous to configure the control unit 12 so as to control the robotised arm 13 such as to prevent the displacement of the tool guide 14 in at least one direction, or to limit the displacement of the tool guide 14 according to a single direction corresponding to the main axis 145 of the tool guide 14 (the direction of release follows the main axis 145 of the tool guide 14 in a direction going from the retention device 146 to the base 142). According to particular embodiments, when the "release cooperative manual control" mode is activated, the control unit 12 is configured to store as the reference position the current position of the tool guide 14 relative to the patient reference 22 position. The reference position is thus the position of the tool guide 14 at a first instant $t_1$ in which the "release cooperative manual control" mode is activated.

A so-called "return cooperative manual control" mode corresponds for example to a mode in which, after the control image has been produced, the robotised arm 13 is displaced manually by the practitioner in order for the tool guide 14 to regain the reference position which had been recorded when the "release cooperative manual control" mode had been selected. This reference position corresponds to the position of insertion 102 (target position which the tool guide 14 must reach). The "return cooperative manual control" mode is thus used to bring the tool guide 14 from the released position 103 to the position of insertion 102, in order to finalise the insertion of the medical instrument 15. It is important that, in its displacement, the tool guide 14 does not go beyond the position of insertion 103 (in other words the tool guide 14 would not be brought to the correct position in order to finalise the insertion, and there would also be a collision between the partly inserted medical instrument and the tool guide 14). It can be advantageous to control the robotised arm 13 such as to limit the displacement of the tool guide 14 in the direction along the main axis 145 of the tool guide 14 (the return direction follows the main axis 145 of the tool guide 14 in a direction going from the base 142 towards the retention device 146). In addition, it can be advantageous to configure the control unit 12 in order to control the speed of displacement of the tool guide 14 according to the distance between the current position of the tool guide 14 and the target position which the tool guide 14 must reach (corresponding to the recorded reference position). Thus, for a second instant $t_2$, the control unit 12 is configured to calculate the difference between the position of the tool guide at the second instant $t_2$ and the reference position (position of the tool guide 14 at the first instant $t_1$). The speed of displacement of the tool guide 14 is controlled such that, the shorter the distance calculated is (i.e. the closer the tool guide 14 is to its target position), the lower the speed of displacement is, until a zero speed is reached when the target position is reached. The control unit 12 is configured to determine whether the difference between the position reached by the tool guide 14 and the reference position is lower than a predetermined threshold. If this is the case, then it is considered that the target position has been reached. It should be noted that the position of the tool guide 14 is defined relative to the position of the patient reference 22 position. When the target position has been reached, the practitioner can finalise the insertion of the medical instrument 15. The predetermined threshold is for example equal to 1 mm, or to one tenth of a millimetre (0.1 mm), or even to three hundredths of a millimetre (0.03 mm).

When a "cooperative manual control" mode is activated, the practitioner displaces the robotised arm 13 by exerting a force with his hand on the tool guide 14. The displacement of the robotised arm 13 is however controlled by the control unit 12, which exerts a force control (control of the speed of displacement of the tool guide 14) and a position control (control of the directions of displacement of the tool guide 14).

The force control is governed by a control law by admittance. The speed of displacement of the tool guide 14 is controlled by the control unit 12. The speed of displacement of the tool guide 14 is calculated according to the force exerted by the practitioner on the tool guide 14, said force being determined by the control unit by means of the force sensor 16.

More specifically, the force thus determined corresponds to an input datum of a control loop. The output datum of this control loop is a Cartesian speed of displacement of the tool guide 14. The control loop is for example operated at a frequency of 125 Hz (in this case, the value of the speed of displacement of the tool guide 14 is updated every 8 ms).

The control unit 12 calculates a speed of displacement of the tool guide 14, making it possible to cancel the force exerted by the practitioner on the tool guide. In other words, the difference (also known as error) between the value of this force determined at a current instant (at each iteration of the control loop) and the required value of the force (zero force) is equal to the force determined. The algorithm of the control loop is designed to define a speed of displacement which makes the error tend towards zero. In order to correct this error, a PID corrector can be used (PID is the acronym for "Proportional, Integral, Derivative". It is a closed-loop control system which is commonly used in industry). The error (i.e. the difference between the force determined and the force required) is the input datum of the PID corrector, which provides as output a speed making it possible to obtain an error which tends towards zero.

Hereinafter, for the sake of simplification, only the "proportional" part of the PID corrector is taken into consideration. In other words, it is as if the "integral" and the "derivative" parts were zero.

The speed of displacement of the tool guide 14 is calculated by applying a gain factor to the force determined:

$$|v| = G \times |f| \qquad \text{[Math. 2]}$$

where G is the gain factor, |f| is the force determined by the control unit (force exerted by the practitioner on the tool guide 14), and |v| is the speed of displacement of the tool guide 14. The gain factor G corresponds to the gain factor of the "proportional" part of the PID corrector.

In other words, the greater the force exerted by the practitioner on the tool guide 14 is, the greater the speed of displacement of the tool guide 14 calculated by the control unit 12 is. Thus, when the tool guide 14 is relatively far from the patient, and the practitioner exerts a substantial force on the tool guide 14, the robotised arm 13 is displaced rapidly, fluidly and reactively. On the other hand, when the practitioner exerts a low-amplitude force on the tool guide 14 because the tool guide 14 is close to the relevant part of the anatomy of the patient, the robotised arm 13 is displaced at a low speed in order to guarantee precision and safety.

When the tool guide 14 is relatively close to the relevant part of the anatomy of the patient, the movement of the tool guide 14 must however be controlled with precision and at a low speed, in order to reach the position of insertion 102 of the medical instrument with exactitude. Thus, it is necessary to avoid jerky movements of the robotised arm 13 caused by trembling by the practitioner. For this purpose, the value of the gain factor is defined such as to be variable according to the force exerted by the practitioner on the tool guide. For example, the gain factor varies linearly together with this force when this force varies between a minimal value $F_{min}$ and a maximal value $F_{max}$. The value of the gain factor G(f) can be defined as follows:

$$G(f) = K \times \left(1 + \frac{|f| - F_{min}}{F_{max} - F_{min}}\right) \text{ if } F_{min} \le |f| \le F_{max} \qquad \text{[Math. 1]}$$

14 where K is a constant, |f| is the force determined by the control unit (force exerted by the practitioner on the tool guide 14), and $F_{min}$ and $F_{max}$ correspond respectively to a minimal value and a maximal value for the force which can be exerted by the practitioner. The gain is undefined if |f| is greater than $F_{max}$: when |f| is greater than $F_{max}$, the speed has a ceiling set at a maximum speed $V_{max}$. The gain is zero if |f| is lower than $F_{min}$: the speed is zero if the force |f| is lower than $F_{min}$.

The fact that the gain factor varies according to the force exerted by the practitioner on the tool guide makes it possible to avoid jerking in the displacement of the robotised arm 13 generated by trembling by the practitioner (the trembling corresponds to a low-amplitude force which varies with a high frequency). The variability of the gain factor according to the force exerted by the practitioner on the tool guide makes it possible to guarantee precision and safety in the displacement of the tool guide 14 when the tool guide 14 is close to the relevant part of the anatomy of the patient. In addition, a definition of this type of the gain factor permits continuity of the speed of displacement of the tool guide 14 when the force exerted by the practitioner on the tool guide varies between $F_{min}$ and $F_{max}$.

As an alternative to what has been described with reference to the equation Math.2, the speed of displacement of the tool guide 14 can also be calculated in the form:

$$|v| = G \times (|f| - F_{min}) \qquad \text{[Math. 3]}$$

FIGS. 8 and 9 describe this in greater detail. FIG. 8 corresponds to a case where the gain factor G is constant when the force exerted by the practitioner on the tool guide determined by the control unit varies between $F_{min}$ and $F_{max}$. FIG. 9 corresponds to a case where the gain factor varies according to the force determined (G is defined as in the expression Math.1). Each of FIGS. 8 and 9 comprises four graphs. The graph in part a) of FIGS. 8 and 9 represents the speed (|v|) of displacement of the tool guide 14 according to the force (|f|) determined. The graph in part b) of FIGS. 8 and 9 represents the acceleration (|a|) which the tool guide 14 undergoes according to the force (|f|) determined. The graph in part c) of FIGS. 8 and 9 represents the force (|f|) determined on a time (t) basis when the practitioner displaces the tool guide 14 with a low-amplitude force varying with high frequency (slow movement with trembling). The graph in part (d) of FIGS. 8 and 9 represents the acceleration (|a|) which the tool guide 14 undergoes on a time (t) basis when the force determined varies as illustrated on the graph of part c) (slow movement with trembling).

In the scenario corresponding to FIG. 8, the gain factor G is constant when the force determined varies between $F_{min}$ and $F_{max}$. The gain factor G is zero when the force determined is lower than $F_{min}$. The speed of displacement of the tool guide 14 has a ceiling set at a maximum speed $V_{max}$ when the force determined is greater than $F_{max}$. As illustrated in part a) of FIG. 8, |v| varies linearly between zero and $V_{max}$ when |f| varies between $F_{min}$ and $F_{max}$. |V| is zero when |f| is lower than $F_{min}$. As illustrated in part a) of FIG. 8, the acceleration |a| which the tool guide 14 undergoes then adopts a constant value A when |f| varies between $F_{min}$ and $F_{max}$. The acceleration |a| which the tool guide 14 undergoes is zero when |f| is lower than $F_{min}$ or greater than $F_{max}$. It is thus shown in part d) of FIG. 8 that, when |f| oscillates around $F_{min}$ (low-amplitude force exerted by the practitioner with trembling, as illustrated in part c) of FIG. 8, then the acceleration |a| which the tool guide 14 undergoes goes suddenly from the value zero to the value A each time the force |f| determined goes above $F_{min}$. Conversely, the acceleration |a| which the tool guide 14 undergoes goes suddenly from the value A to the value zero each time the force |f| determined goes below $F_{min}$. A situation of this type leads to a jerky movement of the tool guide 14.

In the scenario corresponding to FIG. 9, the gain factor G varies linearly together with the force |f| determined when |f| varies between $F_{min}$ and $F_{max}$. The gain factor G is zero when the force determined is lower than $F_{min}$. The speed of displacement of the tool guide 14 has a ceiling set at a maximum speed $V_{max}$ when the force determined is greater than $F_{max}$. As illustrated in part a) of FIG. 9, |v| varies exponentially between zero and $V_{max}$ when |f| varies between $F_{min}$ and $F_{max}$. |v| is zero when |f| is lower than $F_{min}$. As illustrated in part a) of FIG. 9, the acceleration |a| which the tool guide 14 undergoes varies linearly between a minimal value $A_{min}$ and a maximal value $A_{max}$ when |f| varies between $F_{min}$ and $F_{max}$. The acceleration |a| which the tool guide 14 undergoes is zero when |f| is lower than $F_{min}$ or greater than $F_{max}$. It can thus be seen in part d) of FIG. 9 that, when |f| oscillates around $F_{min}$ (low-amplitude force exerted by the practitioner with trembling, as illustrated in part c) of FIG. 9), then the acceleration |a| which the tool guide 14 undergoes goes from the value zero to the value $A_{min}$ each time the force |f| determined goes above $F_{min}$, |a| varies continuously and linearly together with |f| when |f| is greater than $F_{min}$, and |a| goes from the value $A_{min}$ to the value zero each time the force |f| determined goes below $F_{min}$. The value $A_{min}$ is however significantly lower than the value A. The variations of the acceleration |a| which the tool guide 14 undergoes, represented in part d) of FIG. 9, are distinctly slighter than the variations represented in part d) of FIG. 8. Thus, varying the value of the gain factor G according to the force determined makes it possible to avoid jerking in the displacement of the robotised arm 13 generated by trembling by the practitioner.

It should be noted that the definition of the gain factor G proposed by the equation [Math.1] is only a non-limiting example. It will be appreciated that it can be envisaged to define the gain factor G differently, while making it vary according to the force determined. The selection of a particular definition of the gain factor G is only a variant of the invention.

For the position control, the speed calculated at the output of the PID corrector is multiplied by a selection matrix. This selection matrix makes it possible to select the position directions which must be controlled by applying a multiplicative coefficient equal to zero in the prohibited directions, and a multiplicative coefficient equal to one in the permitted directions. The speed which is obtained after application of the selection matrix corresponds to the speed of displacement of the tool guide 14.

As has already previously been mentioned, in the "cooperative manual control" mode, it can be advantageous to configure the control unit 12 to control the robotised arm 13 such as to prevent the displacement of the tool guide 14 in at least one direction, or to limit the displacement of the tool guide 14 according to a single direction corresponding to the main axis 145 of the tool guide 14, in particular in order to release the tool guide 14 in the released position 103 ("release cooperative manual control" mode), or to bring the tool guide 14 from the released position 103 to the position of insertion 102 ("return cooperative manual control" mode).

Also, as has also previously been mentioned for the "return cooperative manual control" mode, it can be advantageous to configure the control unit 12 to control the speed of displacement of the tool guide 14 according to the distance between the current position of the tool guide 14 and the target position which the tool guide 14 must reach. The speed of displacement of the tool guide 14 can in particular be controlled such that, the shorter this distance is (i.e. the closer the tool guide 14 is to its target position), the slower the speed of displacement is, until a zero speed is reached when the target position is reached.

For the "approach cooperative manual control" mode, there is no position control: the displacement of the tool guide 14 is not constrained in any direction. Only force control is applied in this mode.

The control unit 12 of the medical robot 10 can also be configured to detect a situation of risk of injury by the medical instrument 15, for example when the patient 20 makes an unexpected movement while the medical instrument 15 is not yet released from the tool guide. In fact, a situation of this type can lead to injury of the patient by the medical instrument (for example damage to the healthy tissue of the relevant part of the anatomy or another part of the body of the patient, by the medical instrument). Measures can thus be taken to prevent the patient from being injured when a situation of this type is detected.

In particular embodiments, the tool guide 14 of the medical robot 10 comprises an actuator which makes it possible to release the medical instrument 15 instantaneously. The actuator is controlled by the control unit 12 of the medical robot, in order to move apart the two movable parts of the retention device 146, thus releasing the medical instrument 15. The control unit 12 is configured to command the tool guide 14 to release the medical instrument 15 when a particular situation of risk of injury is detected.

According to a first example, a particular situation of risk of injury is detected when the control unit 12 receives information obtained from the navigation system 30, indicating unexpected displacement of the patient reference 22 (change of position of the patient reference 22 which is representative of an unexpected movement by the patient 20).

According to a second example, a "medical instrument insertion" mode can be selected via the user interface, and activated via the control pedal 19. In this mode, the control unit 12 is configured to prevent any displacement of the tool guide 14, and the control unit 12 is configured to determine by means of the force sensor a force exerted on the medical instrument 15. A particular situation of risk of injury is for example detected when the force exerted on the medical instrument is greater than a predetermined threshold value (an unexpected movement by the patient 20 has the consequence of exerting a force on the force sensor 16 via the medical instrument 15). According to another example, a particular situation of risk of injury is detected when a variation of the force exerted on the medical instrument over a given period of time is greater than a predetermined threshold value.

The automatic release of the medical instrument 15 can be accompanied by an automatic release of the robotised arm 13 in the direction of release (direction along the main axis 145 of the tool guide 14 towards the base 11 of the medical robot).

The above description illustrates clearly that, by means of its different characteristics and their advantages, the present invention achieves the objectives set out.

In particular, the fact of defining the speed of displacement of the tool guide 14 on the basis of a gain factor which varies according to the force exerted by the practitioner permits controlled, precise and smooth displacement of the robotised arm 13 when the practitioner displaces the tool guide 14 manually by exerting a low-amplitude force. The displacement of the robotised arm 13 continues to be fluid and reactive when the practitioner exerts a high-amplitude force on the tool guide 14.

The force control and position control of the robotised arm 13 make it possible to release the tool guide 14 in a safe manner after an (optionally partial) insertion of the medical instrument 15. If necessary, the invention also makes it possible to bring the tool guide 14 to the position of insertion safely and precisely.

Finally, the automatic emergency release of the medical instrument 15 makes it possible to avoid injuring the patient when the patient makes an unexpected movement during the medical procedure.

It should be noted that the invention has been described using an optical navigation system. However, according to a variant, nothing would prevent use of an electromagnetic navigation system in the place of the optical navigation system. In this case, the different "markers" which can be detected by the navigation system (markers present on the patient reference 22, markers present on the tool guide 14) would then correspond to electromagnetic sensors, the position of which can be determined by the navigation system in an electromagnetic field generated.

The invention claimed is:

1. A medical robot to assist a practitioner during a medical procedure on a relevant part of the anatomy of a patient, said medical robot comprising a robotized arm comprising at a distal end a tool guide which is designed to guide a medical instrument, as well as a control unit which is configured to control the displacement of the robotised arm, said tool guide being coupled to a force sensor, and, when the medical robot is used in a cooperative manual control mode, the control unit is configured to:

determine, by means of the force sensor, a force exerted by the practitioner on the tool guide;

calculate a speed of displacement of the tool guide according to a gain factor applied to said force thus determined; and control the displacement of the robotized arm according to the speed thus calculated, wherein the value of said gain factor is variable, and calculated according to said force which is exerted by the practitioner on the tool guide.

2. The medical robot of claim 1, wherein the gain factor corresponds to a proportional parameter of a Proportional, Integral, Derivative corrector implemented by the control unit.

3. The medical robot of claim 1, wherein the control unit is also configured to prevent the displacement of the tool guide in at least one direction.

4. The medical robot of claim 1, wherein the control unit is also configured to limit the displacement of the tool guide in a single direction corresponding to a main axis of the tool guide.

5. The medical robot of claim 1, wherein the value of the gain factor is defined thus:

$$G(f) = K \times \left(1 + \frac{|f| - F_{min}}{F_{max} - F_{min}}\right) \text{ if } F_{min} \leq |f| \leq F_{max}$$

where G(f) is the gain factor; K is a constant; |f| is the force exerted by the practitioner on the tool guide, determined by the control unit by means of the force sensor, $F_{min}$ and $F_{max}$ correspond respectively to a minimal value and a maximal value for the force exerted by the practitioner.

6. The medical robot of claim 1, wherein the control unit is configured to calculate the speed of displacement of the tool guide also according to a distance between a current position of the tool guide and a target position which the tool guide must reach.

7. The medical robot of claim 1, wherein the robotized arm is an articulated arm with at least six degrees of freedom.

8. The medical robot of claim 1, wherein, when the medical robot is being used in a medical instrument insertion mode, the control unit is configured to prevent any displacement of the tool guide, and, by means of the force sensor, the control unit is configured to determine a force exerted on the medical instrument, the tool guide comprises means to release the medical instrument automatically at a command from the control unit, and the control unit is configured to command the tool guide to release the medical instrument when the force exerted on the medical instrument is greater than a predetermined threshold value, or when a variation of the force exerted on the medical instrument over a given period of time is greater than a predetermined threshold value.

9. The medical robot of claim 1, wherein the tool guide comprises at least one marker which can be detected by a navigation system, and the control unit is configured to:

receive from said navigation system a first piece of information relating to a position of the tool guide in a reference of the navigation system;

receive from said navigation system a second piece of information relating to a target position, in the reference of the navigation system, which the tool guide must reach;

determine the target position, in a reference of the medical robot, by means of the second piece of information; and displace the robotized arm, in an automatic control mode, without the intervention of the practitioner, in order for the tool guide to reach the target position.

10. The medical robot of claim 9, wherein the second piece of information corresponds to a position, in the reference of the navigation system, of a patient reference which is designed to be positioned on the patient in the vicinity of the relevant part of the anatomy, said patient reference comprising at least one marker which can be detected by the navigation system, and at least one radio-opaque marker, and the control unit is configured to determine the target position of the tool guide from the position of the patient reference and from a trajectory which the medical instrument must follow in order to carry out the medical intervention, said trajectory being defined relative to the position of the patient reference by means of a pre-intervention medical image on which there can be seen the relevant part of the anatomy of the patient and said at least one radio-opaque marker of the patient reference.

11. The medical robot of claim 10, wherein the control unit is configured to:

store as the reference position a position at a first instant of the tool guide relative to the position of the patient reference; and determine whether a difference between a position at a second instant of the tool guide and the reference position is lower than a predetermined threshold.

12. The medical robot of claim 10, wherein the tool guide comprises means for releasing the medical instrument automatically at the command of the control unit, and the control unit is configured to command the tool guide to release the medical instrument when the control unit receives information from the navigation system indicating an unexpected displacement of the patient reference.

\*   \*   \*   \*   \*